United States Patent [19]
Beckstein et al.

[11] 4,255,050
[45] Mar. 10, 1981

[54] APPARATUS FOR MEASURING THE POSITION OF WEFT THREADS IN A MOVING FABRIC WEB

[75] Inventors: Hellmut Beckstein, Bad Abbach; Guenter Schellenberger, Saal, both of Fed. Rep. of Germany

[73] Assignee: Mahlo GmbH & Co. KG, Saal, Fed. Rep. of Germany

[21] Appl. No.: 88,175

[22] Filed: Oct. 25, 1979

[30] Foreign Application Priority Data

Nov. 23, 1978 [DE] Fed. Rep. of Germany ....... 2850804

[51] Int. Cl.$^3$ ...................... D06M 3/12; G01B 11/26
[52] U.S. Cl. .................... 356/238; 26/51.5; 250/563; 356/429
[58] Field of Search ............... 356/238, 242, 429, 430, 356/431; 250/548, 561, 562, 563, 559; 26/51.5

[56] References Cited

U.S. PATENT DOCUMENTS

| | | | |
|---|---|---|---|
| 2,219,213 | 10/1940 | Swain | 250/561 |
| 2,972,794 | 2/1961 | Saul et al. | 26/51.5 |
| 3,193,688 | 7/1965 | Morton et al. | 356/238 |
| 3,517,204 | 6/1970 | Mahlo et al. | 356/238 |

FOREIGN PATENT DOCUMENTS

1124493 8/1968 United Kingdom ..................... 356/429

Primary Examiner—Richard A. Rosenberger
Attorney, Agent, or Firm—W. G. Fasse; D. F. Gould

[57] ABSTRACT

The deviation of the weft threads in a fabric is ascertained to show the extent and angle of the deviation relative to a line extending at a right angle relative to the edge of a moving fabric web. For this purpose a sensor head or several sensor heads are movable across the web. Separate signals are produced for the left and right half of the web relative to a longitudinal center line of the web. A comparing unit compares the separate signals for forming a control value or signal.

8 Claims, 4 Drawing Figures

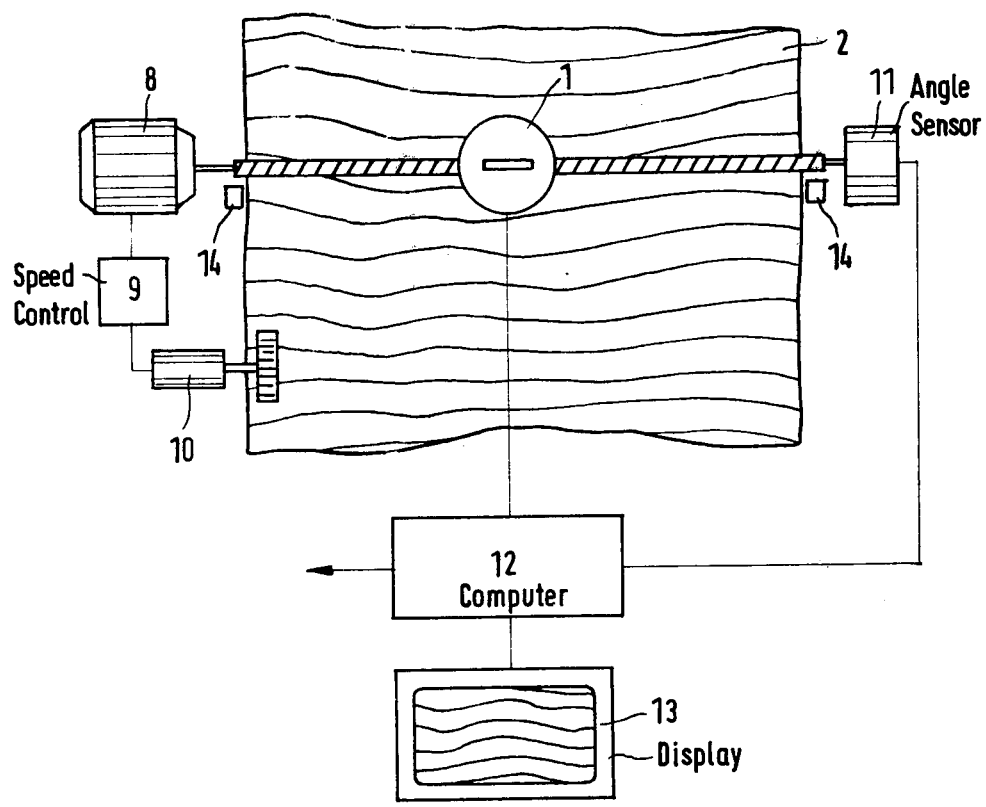

APPARATUS FOR MEASURING THE POSITION OF WEFT THREADS IN A MOVING FABRIC WEB

BACKGROUND OF THE INVENTION

The invention relates to an apparatus for measuring the position of weft threads in a moving fabric or textile web, whereby to ascertain deviations of the fabric web from a standard, said deviations being indicated by an angular measurement and by a length measurement. German Pat. 1,635,266 discloses an apparatus for measuring the position of the weft threads in a travelling textile or fabric web by means of one or several sensor heads which ascertain deviations of the fabric or textile web by an angular measurement and by a length measurement. In this prior art device each sensor head scans only a fraction of the total length of the web threads or of the mesh rows or the like, whereby the angle is ascertained which this fractional length of the entire weft thread length takes up relative to a normal position. Such scanning of short weft thread lengths is sufficient for recognizing the entire characteristic of uniform deviations. Thus, it is possible with the prior art apparatus to ascertain with a single scanning or sensor head uniform, steady, slanting deviations. Uniform, bent bow-shaped deviations require at least two scanning heads arranged symmetrically relative to the center of the fabric web. In both instances the deviation is determined with regard to its direction and with regard to its value without any difficulty.

However, where the deviations are not uniform, but rather non-symmetric or wavy, as happens frequently in practice, and where the deviations are composed of bow-shaped components as well as slanted components, the prior art apparatus is not capable of providing an information regarding the actual weft thread course unless a combination of a plurality of sensing heads uniformly distributed over the width of the fabric web is employed for obtaining such information. The certainty or rather the accuracy of the result increases with the number of sensing heads.

Certain types of textiles such as coarse curtain textiles, canvas, textile wall coverings and the like are structured so loosely that especially any treatment of the fabrics in the non-spread out condition may easily cause a waviness of the weft threads in the weft direction. Such waviness may, for example, occur when the fabric is subjected to bleaching while still in a hang or when the fabric is exposed to humidity. Such waviness may be so large and have such a short wave length that a reliable scanning with a limited number of scanning heads becomes practically impossible.

OBJECTS OF THE INVENTION

In view of the above it is the aim of the invention to achieve the following objects singly or in combination:
to provide an apparatus which is capable of ascertaining the entire course of the weft threads even if the latter are subject to locally very non-uniform wavy, deviations;
to measure the weft deviations even if the latter are completely unsymmetric and even if the deviations combine all types of deviations such as bow-shaped deviations, slanted deviations, and waviness; and
to achieve the foregoing objectives with a minimum number of scanning heads.

SUMMARY OF THE INVENTION

According to the invention the above objectives are achieved by movably supporting one or several scanning heads for movement across the entire width of the fabric weft and that a comparing device is provided which compares the signals derived on one side of a longitudinal center line of the fabric web with the signals derived on the other side of said center line of the fabric. Said center line runs so as to divide the fabric web into two halfs. A control value such as a control signal is produced from such comparing.

According to the invention it is even possible to use but one sensor or scanning head which is moved sufficiently rapidly across the feed advance direction of the fabric web and which activates a switch-over means in the center of the fabric web to produce two sets of signals, one set for each half of the fabric web. In another embodiment of the invention several scanning heads are used which are movable symmetrically relative to the center and across the fabric web.

The output signals of these scanning heads are integrated and evaluated over the entire length of the cross movement or over portions of such cross movement. The evaluated signals serve primarily for controlling of machines for correcting, or rather straightening, the fabric structure, whereby such machines are located downstream of the measuring device. Such straightening machines are well known in the art and they may employ tiltable or curved rollers for the straightening by partially varying the speed of the rollers over which the textile web is travelling. Such machines are also known which employ different speeds of two chains carrying the fabric web, for example, by forming tentering frames, whereby the deviations of the fabric web are removed. If separate, symmetrically arranged straightening machines are used, the two halves of the fabric web are also separately scanned on both sides of the fabric web relative to the fabric center line.

BRIEF FIGURE DESCRIPTION

In order that the invention may be clearly understood, it will now be described, by way of example, with reference to the accompanying drawings, wherein:

FIG. 4 is a further embodiment according to the invention employing but one scanning head movable across the entire fabric web and cooperating with an angle sensor and computer as well as display means.

DETAILED DESCRIPTION OF PREFERRED EXAMPLE EMBODIMENTS AND OF THE BEST MODE OF THE INVENTION

Figure 1:
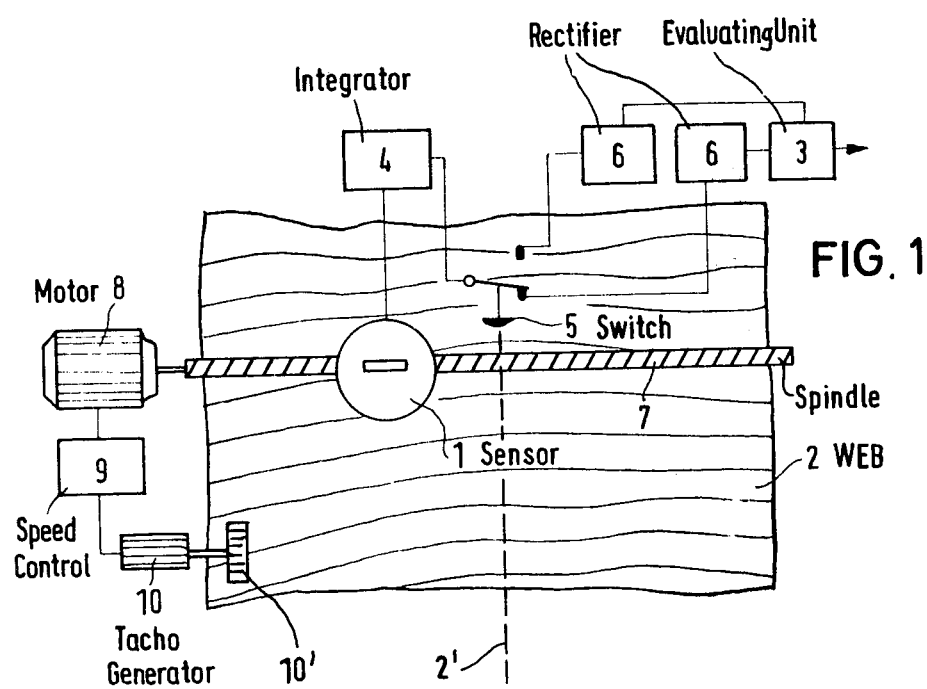
FIG. 1 is a schematic top plan view of a portion of a fabric web and of an embodiment of the invention employing one scanning or sensor head which is movable across both halves of the fabric web.

FIG. 1 shows the arrangement of one scanning or sensor head 1 which according to the invention is driven by means of a threaded spindle 7 and a motor 8, whereby the direction of rotation of the spindle 7 is periodically reversed to move the scanning head 1 across the fabric web 2 alternately in opposite directions. The output signal of the scanning head 1 is integrated in the summing or integrating network 4. When the scanner 1 passes the center line 2' of the fabric web 2, a switch 5 switches the output of the integrator 4 to the other of the two rectifiers 6, both of which are connected with their outputs to a signal evaluating circuit arrangement 3. Thus, one of the rectifiers is effective when the scanner 1 moves across the left half of the fabric web while the other rectifier is effective when the scanner moves across the other half of the fabric web. The travelling speed of the scanner or sensor head 1 may be controlled by varying the r.p.m. of the motor 8 by means of a conventional speed control 9 which is responsive to a tacho-generator 10, the output of which depends on the tension of the fabric web 2 which tension is sensed by a sensing wheel 10' operatively connected to the tacho-generator 10. Thus, the scanning speed may be adapted to the travelling speed of the fabric web.

Figure 2:
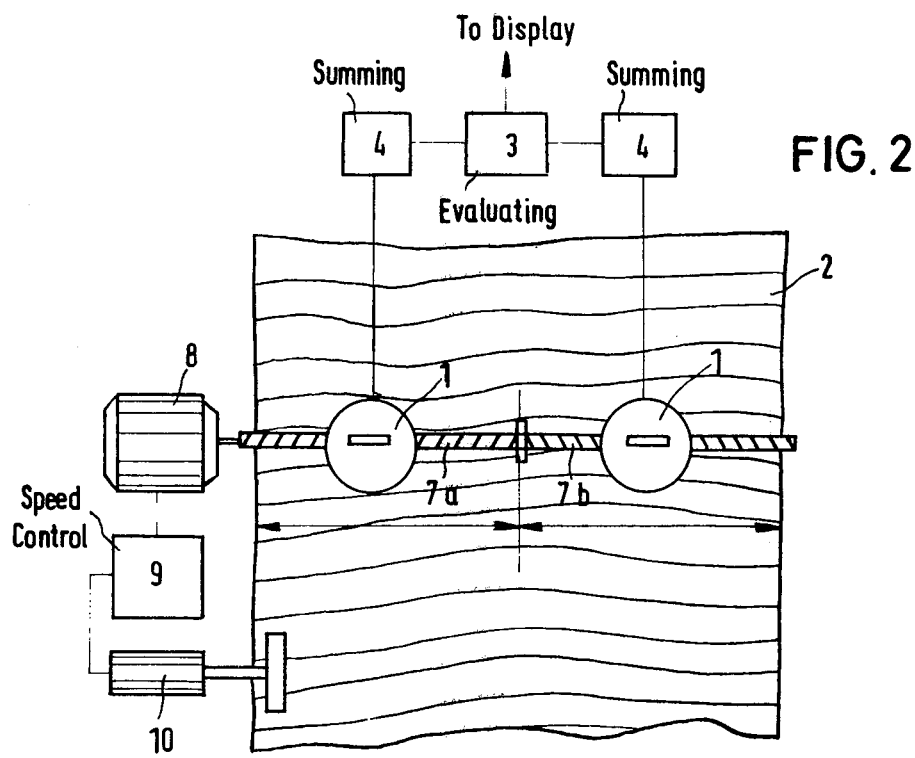
FIG. 2 is a view similar to that of FIG. 1, however, showing an embodiment of the invention with two scanning heads, each movable across its own half of the fabric web.

FIG. 2 illustrates the simultaneous cross movements of two scanning heads 1 supported on oppositely threaded spindles 7a and 7b. Each output of each scanning head 1 is operatively connected to a respective summing network 4. Both summing networks 4 are connected to the signal evaluating circuit 3 which comprises a conventional comparator for producing a control signal. The control signal in turn, just as in FIG. 1, is used to straighten the fabric by equipment not shown since it is not part of the invention. In FIG. 2 again the adaptation of the scanning speed to different web travelling speeds is accomplished by the tacho-generator 10 and a control circuit 9 for the motor 8 which drives both spindles 7a and 7b.

Figure 3:
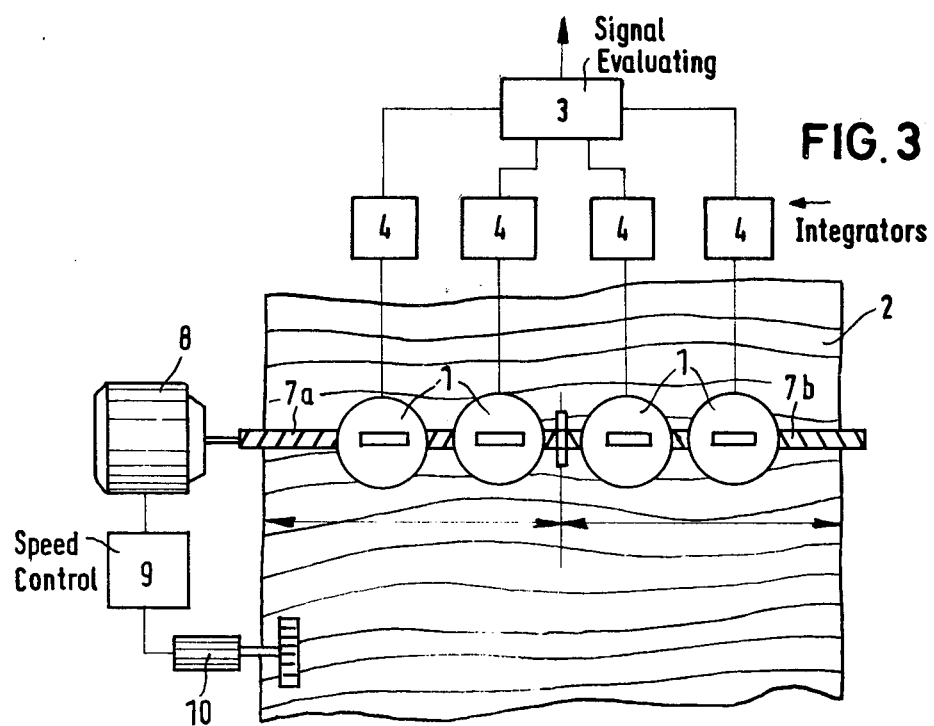
FIG. 3 is a top plan view of a further embodiment of an apparatus according to the invention employing four scanning heads movable across the width of the fabric web.

FIG. 3 represents a modification of the embodiment of FIG. 2 in which simultaneously two scanning heads 1 move across each half of the fabric web. The signal evaluation is the same as in FIG. 1 and in FIG. 2. Each scanning head 1 is provided with its respective summing network 4.

The signal evaluation of the output signals of each individual scanning head may be accomplished in principle in the manner shown in FIGS. 1 to 3, whereby substantially summing or integration networks and mixing stages as well as comparators are provided which continuously compare the information derived from one side or half of the fabric thread with the information derived from the other side of the fabric web. However, it is also possible to evaluate the signal in such a manner that the deviation representing signals are correlated to the respective position in a coordinate type of system and supplied to a computer where the signals are stored. From the signals stored in the computer, control signals may be derived which may be used for controlling any type of straightening mechanism, for example, a straightening mechanism which is effective locally or which is effective only during a limited time. Such straightening devices may also be effective in a non-symmetric manner. Further, it is possible to display the deviations ascertained as a result of the cross motions of the scanner relative to each location along the fabric width. For this purpose a computer supplies the respective deviation representing signals to a display screen such as a cathode-ray tube or the like.

FIG. 4 illustrates an embodiment with a display screen 13 controlled by the computer 12 which receives the output signal from the scanner 1 and a further signal derived from an angle sensor 11. The scanner 1 is again driven by the motor 8 through the spindle 7 to move back and forth across the fabric web 2. The speed of this cross movement is again correlated to the travelling speed of the fabric 2 by means of a tacho-generator 10 and the speed control circuit 9. The angle sensor 11 is connected to the spindle 7, whereby the angle sensor 11 provides a signal which is proportional to the spindle position and thus to the position of the scanning head 1. The computer 12 receives, as mentioned, the output signals from the scanning head 1 as well as the output signal from the angle sensor 11 and forms in accordance with the respective programming the control signals which are necessary for the removal of the respective deviation or rather, necessary for straightening the fabric web. The programming, which is not part of the invention, is tailored to the respective control mechanism. Simultaneously, with the straightening control the screen 13 may display a direct picture, reduced in scale, of the weft thread paths, whereby the display may receive the respective signals from a memory forming part of the computer and the display of the weft pattern is a continuous type of operation.

In order to increase the scanning speed it is possible to use a mechanism in which several scanning heads are arranged to scan sections of the fabric web width, whereby the output signals of these sectional scanners are read by the computer 12 which in turn arranges these signals in response to the position representing signals received from the angle sensor 11, whereby the evaluation of these signals is then dependent on the respective position of the corresponding sectional scanning member.

The speed of ascertaining the information depends on the speed of the scanning motion across the web. An optimal solution in this respect would be the arrangement of fixed scanning heads without any gaps therebetween across the width of the fabric. However, it is not possible to realize this type of arrangement in practice due to unjustifiably large expenses. If only one scanning head is moved across the web 2 as shown in FIGS. 1 and 4, it is necessary to move such head rapidly enough so that a control signal may be formed from the derived scanning signal. The control signal must be obtained rapidly enough to cause the straightening operations in a sufficiently short time, that is without any noticeable dead time and having regard to the given operational speed of the machine. Thus, devices employing several scanning heads each of which covers only a portion or section of the web width and which together provide for the formation of the control signal, are preferable. Nevertheless, the invention is operable with a low number of scanning heads as compared to prior art requirements.

Although in the illustrated example embodiments the scanning heads are driven by respective threaded spindles, it will be appreciated that the scanning heads may also be driven by chain drive means, by rope or pulley drives, by toothed racks or by pneumatic piston cylinder arrangements or other similar devices. The invention is also not limited to the back and forth movement. Rather, it is also possible to move the scanning heads along an endless path.

For the control of the cross motion range and the travelling speed of the scanners it is possible to use simple limit switch means which are shown symbolically at 14 in FIG. 4. Such limit switch means cause the reversal of the movement direction of the scanner 1 and are well known in the art in many different types. For example, photo-electric limit switch means, pneumatic or mechanical edge sensors could be used for limiting the movement of the sensor heads 1 at the edges of the fabric and for reversing the movement direction. Such reversing may also be accomplished by electro-mechanical or electronic devices which may be programmed in accordance with the respective width of the fabric to accommodate or adapt the cross motion to the fabric width. The adjustment of the end sensors may be accomplished manually or automatically, for example, by photo-electric means. The scanning speed, that is, the cross motion shall be maintained in a fixed ratio relative to the feed advance speed of the fabric web. For this purpose it is advantageous to control the cross motion by means of a tacho-generator as described.

Although the invention has been described with reference to specific example embodiments, it will be appreciated, that it is intended to cover all modifications and equivalents within the scope of the appended claims.

What is claimed is:

1. An apparatus for measuring the position of weft threads in a moving fabric web having a given width, comprising sensor head means, support means movably supporting said sensor head means for movement across said given width of said fabric web, drive means operatively connected to said sensor head means for effecting said movement, said sensor head means providing a first set of signals representing the weft thread deviation on one side of a longitudinal center line of said fabric web and a second set of signals representing the weft thread deviation on the other side of said center line, said apparatus further comprising signal evaluating means operatively connected to said sensor head means for comparing said first and second sets of signals to produce a control value.

2. The apparatus of claim 1, wherein said sensor head means comprise a single sensor head, said apparatus further comprising switch-over means operatively arranged substantially at said center line so that said single sensor head delivers both sets of signals.

3. The apparatus of claim 1, wherein said sensor head means comprise at least two sensor heads one of which is operatively arranged on one side of said center line whereas the other sensor head is operatively arranged on the other side of said center line, said drive means being operatively connected to said sensor head means for moving the sensor head means on one side of the center line in a direction opposite to the direction of moving the sensor head means on the other side of said center line, said apparatus further comprising summing circuit means operatively connected to the respective sensor head means for summing the signals of the respective signal set, said signal evaluating means comprising signal mixing means and signal comparing means for producing said control value.

4. The apparatus of claim 3, wherein said signal evaluating means comprise computer means operatively connected to said sensor head means, said apparatus further comprising angle sensor means also operatively connected to said computer means for processing in said computer means said deviation representing signals from said sensor head means and position representing signals from said angle sensor means.

5. The apparatus of claim 1, further comprising display means operatively connected to said signal evaluating means for displaying the position of said weft threads.

6. The apparatus of claim 1, wherein said signal evaluating means provide a control signal for controlling the operation of deviation correcting means.

7. The apparatus of claim 1, wherein said drive means comprise threaded spindle means for moving said sensor head means.

8. The apparatus of claim 1, further comprising limit stop means operatively arranged alongside each edge of said fabric web for limiting the movement of said sensor head means.

* * * * *